(12) United States Patent
Aissaoui et al.

(10) Patent No.: US 7,538,109 B2
(45) Date of Patent: May 26, 2009

(54) QUINOXALIN-3-ONE DERIVATIVES AS OREXIN RECEPTOR ANTAGONISTS

(75) Inventors: Hamed Aissaoui, Pulversheim (FR); Martine Clozel, Binningen (CH); Thomas Weller, Binningen (CH); Ralf Koberstein, Lörrach (DE); Thierry Sifferlen, Guewenheim (FR)

(73) Assignee: Actelion Pharmaceuticals Ltd, Allschwil (CH)

( * ) Notice: Subject to any disclaimer, the term of this patent is extended or adjusted under 35 U.S.C. 154(b) by 407 days.

(21) Appl. No.: 10/555,061

(22) PCT Filed: Apr. 26, 2004

(86) PCT No.: PCT/EP2004/004374

§ 371 (c)(1),
(2), (4) Date: Oct. 28, 2005

(87) PCT Pub. No.: WO2004/096780

PCT Pub. Date: Nov. 11, 2004

(65) Prior Publication Data

US 2007/0027157 A1   Feb. 1, 2007

(30) Foreign Application Priority Data

Apr. 28, 2003  (EP)  .................. 03/04491

(51) Int. Cl.
*A01N 43/58*  (2006.01)
*A61K 31/50*  (2006.01)
*A01N 43/60*  (2006.01)
*A61K 31/495*  (2006.01)
*C07D 241/36*  (2006.01)

(52) U.S. Cl. ....................... 514/249; 544/354
(58) Field of Classification Search ................ None
See application file for complete search history.

(56) References Cited

FOREIGN PATENT DOCUMENTS

| WO | WO-99/09024 | 2/1999 |
|---|---|---|
| WO | WO-99/58533 | 11/1999 |
| WO | WO-00/47576 | 8/2000 |
| WO | WO 00/47577 * | 8/2000 |
| WO | WO-00/47577 A1 | 8/2000 |
| WO | WO-00/47580 A1 | 8/2000 |
| WO | WO-01/68609 A1 | 9/2001 |
| WO | WO-01/96302 A1 | 12/2001 |
| WO | WO-02/44172 A1 | 6/2002 |
| WO | WO-02/051838 A1 | 7/2002 |
| WO | WO-02/089800 A2 | 11/2002 |
| WO | WO-02/090355 A1 | 11/2002 |
| WO | WO-03/002559 A2 | 1/2003 |
| WO | WO-03/002561 A1 | 1/2003 |
| WO | WO-03/032991 A1 | 4/2003 |
| WO | WO-03/037847 A1 | 5/2003 |
| WO | WO-03/041711 A1 | 5/2003 |
| WO | WO-03/051872 A1 | 6/2003 |
| WO | WO-03/051873 A1 | 6/2003 |
| WO | WO-2004/004733 A1 | 1/2004 |

OTHER PUBLICATIONS

Dorwald F. A. Side Reactions in Organic Synthesis, 2005, Wiley: VCH, Weinheim p. IX of Preface.*
H. Abdel-Ghany, et al.; "A Novel Syntheses of Pyrano(2,3-c)(1,5)Benzodiazepines"; Synthetic Communications; vol. 20(6); 1990; pp. 893-900.
Richard M. Chemelli, et al.; "Narcolepsy in orexin Knockout Mice: Molecular Genetics of Sleep Regulation"; Cell; vol. 98; Aug. 20, 1999; pp. 437-451.
A.M. Farghaly, et al.; "Synthesis of 3-Aryl-2-Substituted-4(3H)-Quinazolines as Potential Antimicrobial Agents"; Il Farmaco; vol. 45(4); 1990; pp. 431-438.
Diana G. Bekerman, et al.; "Comparative Kinetic Studies on the Synthesis of Quinoxalinone Derivatives and Pyrido[2,3-b]pyrazinone Derivatives by the Hinsberg Reaction"; J. Heterocyclic Chem.; vol. 29; Jan.-Feb. 1992; pp. 129-133.
M. F. Ismail, et al.; "Reaction of 6,8-Dibromo-2-methyl-3, 1-benzoxazin-4(H)-one with Some Nucleophilic Reagents: Synthesis of Quinazaoline, Tetrazole & Benzimidazole Derivatives"; Indian Journal of Chemistry; vol. 20B; May 1981; pp. 394-397.
Jozsef Kokosi, et al.; "Nitrogen Bridgehead Compounds Part 90. An Efficient Versatile Synthesis of 1-Methyl-2-Substituted 1,2,3,4-Tetrahydro-6H-Pyrazino[2,1-b]Quinazoline-3,6-Diones"; Heterocycles; vol. 48(9); 1998; pp. 1851-1866.
David S. Lawrence, et al.; "Structure-Activity Studies of Substituted Quinoxalinones as Multiple-Drug-Resistance Antagonists"; J. Med. Chem.; vol. 44; 2001; pp. 594-601.
"Aliphatic Nucleophilic Substitution"; p. 418.

(Continued)

*Primary Examiner*—James O Wilson
*Assistant Examiner*—Jeffrey H Murray
(74) *Attorney, Agent, or Firm*—Hoxie & Associates, LLC; Brittany La

(57) ABSTRACT

The invention relates to quinoxalinone derivatives of general Formula (I) and their use as active ingredients in the preparation of pharmaceutical compositions. The invention also concerns related aspects including processes for the preparation of the compounds, pharmaceutical compositions containing one or more of those compounds and especially their use as orexin receptor antagonists. General Formula (I) wherein X and $R^1$-$R^9$ are as defined in the description

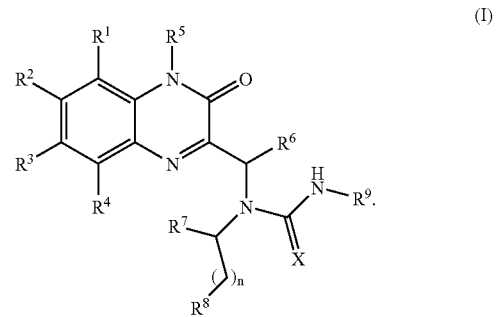

6 Claims, No Drawings

OTHER PUBLICATIONS

Hiroyuki Obase, et al.; "Synthesis of (1-Substituted Piperidin-4-yl)-1H-benzimidazoles and (1-Substituted Piperidin-4-yl)-3,4-dihydroquinazolines as Possible Antihypertensive Agents"; J. Heterocyclic Chem.; vol. 20; May-Jun. 1983; pp. 565-573.

Takeshi Sakurai, et al.; "Orexins and Orexin Receptors: A Family of Hypothalamic Neuropeptides and G Protein-Coupled Receptors that Regulate Feeding Behavior"; Cell.; vol. 92; Feb. 20, 1998; pp. 573-585.

Karnail S. Atwal, et al.; "A Facile Synthesis of Cyanoguanidines From Thioureas"; Tetrahedron Letters; vol. 30(52); 1989; pp. 7313-7316.

* cited by examiner

QUINOXALIN-3-ONE DERIVATIVES AS OREXIN RECEPTOR ANTAGONISTS

The present invention relates to novel quinoxalinone derivatives of the general formula (I) and their use as pharmaceuticals. The invention also concerns related aspects including processes for the preparation of the compounds, pharmaceutical compositions containing one or more compounds of the general formula (I), and especially their use as orexin receptor antagonists.

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also proposed that orexins regulate states of sleep and wakefulness opening potentially novel therapeutic approaches for narcoleptic patients (Chemelli R. M. et al., Cell, 1999, 98, 437-451). Two orexin receptors have been cloned and characterized in mammals. They belong to the super family of G-protein coupled receptors (Sakurai T. et al., Cell, 1998, 92, 573-585): the orexin-1 receptor ($OX_1$) is selective for OX-A and the orexin-2 receptor ($OX_2$) is capable to bind OX-A as well as OX-B.

Orexin receptors are found in the mammalian brain and may have numerous implications in pathologies such as depression; anxiety, addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; cardiovascular diseases; diabetes; appetite/taste disorders; vomiting/nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kaliman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, and angina; urinary bladder incontinence e.g. urge incontinence; tolerance to narcotics or withdrawal from narcotics; sleep disorders; migraine; sleep apnea; narcolepsy; insomnia; parasomnia; jet-lag syndrome; and neurodegenerative disorders including nosological entities such as disinhibition-dementia-parkinsonism-amyotrophy complex; pallido-ponto-nigral degeneration epilepsy; seizure disorders and other diseases related to general orexin system dysfunction.

Up to now some low molecular weight compounds are known which have a potential to antagonise either specifically $OX_1$ or $OX_2$, or both receptors at the same time. In WO 99/09024, WO 99/58533, WO 00/47576, WO 00/47577 and WO 00/47580 formerly SmithKline Beecham reported phenylurea, phenylthiourea and cinnamide derivatives as $OX_1$ selective antagonists. More recently WO 01/85693 from Banyu Pharmaceuticals has been published wherein N-acyltetrahydroisoquinoline derivatives are disclosed. 2-Amino-methylpiperidine derivatives (WO 01/96302), 3-aminomethyl-morpholine derivatives (WO 02/44172) and N-aroyl cyclic amines (WO 02/090355, WO 02/089800 and WO 03/051368) have been suggested by formerly Smith-Kline Beecham as orexin receptor antagonists. Related compounds are disclosed in WO 03/002559, WO 03/002561, WO 03/051873, WO 03/032991 and WO 03/041711. Furthermore benzamide derivatives (WO 03/037847) and ethylene diamine derivatives (WO 03/051872) have been published by SmithKline Beecham. International patent applications WO 01/68609 and WO 02/051838 disclose 1,2,3,4-tetrahydroisoquinoline and novel benzazepine derivatives as orexin receptor antagonists.

The present invention comprises quinoxalinone derivatives, which are non-peptide antagonists of the human orexin receptors. These compounds, therefore, are of potential use in the treatment of disturbed homeostasis and eating disorders (e.g. bulimia, obesity, food abuse, compulsive eating) or irritable bowel syndrome, as well as disturbed sleep/wake schedule, sleep disorders (e.g. insomnias, apneas, dystonias) or stress-related diseases (e.g. anxiety, mood and blood pressure disorders) or any other diseases related to the orexin dysfunction.

The present invention relates to novel quinoxalinone derivatives of the general formula (I).

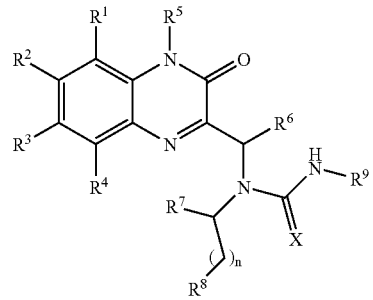

General Formula (I)

wherein:
X is O, NH, N—CN;
n is the integer 0, 1, 2, 3;
m is the integer 0, 1, 2, 3;
$R^1$, $R^2$, $R^3$, $R^4$ independently represent cyano, halogen, hydrogen, hydroxyl, $C_1$-$C_5$ alkyl, $C_2$-$C_5$ alkenyl, $C_1$-$C_5$ alkoxy, $C_2$-$C_5$ alkenyloxy, trifluoromethoxy, cycloalkyloxy or $R^1$ and $R^2$ together as well as $R^2$ and $R^3$ together or $R^3$ and $R^4$ together may form with the phenyl ring to which they are attached, a five, six or seven-membered ring containing one or two oxygen atoms which are separated by at least one carbon atom;

$R^5$ represents hydrogen, $C_1$-$C_5$ alkyl, $C_2$-$C_5$ alkenyl, cycloalkyl, cycloalkyl-$C_1$-$C_5$ alkyl, —$(CH_2)_m$—O—$C_1$-$C_5$ alkyl, —$(CH_2)_m$—COOH, —$(CH_2)_m$—$CO_2$—$C_1$-$C_5$ alkyl, —$(CH_2)_m$—$CONH_2$, —$(CH_2)_m$—CONH—$C_1$-$C_5$ alkyl, —CON—$(C_1$-$C_5$ alkyl$)_2$, —$(CH_2)_m$—N—$C_1$-$C_5$ alkyl;

$R^6$ represents hydrogen, $C_1$-$C_5$ alkyl, cycloalkyl, cycloalkyl-$C_1$-$C_5$ alkyl;

$R^7$ represents hydrogen; $C_1$-$C_5$ alkyl; $C_2$-$C_5$ alkenyl; or mono-, di- or tri-substituted phenyl or phenyl-$C_1$-$C_5$ alkyl, whereby the substituents independently are $C_1$-$C_5$ alkyl, $C_1$-$C_5$ alkoxy, $C_2$-$C_5$ alkenyl or halogen; —$(CH_2)_m$—OH; —$(CH_2)_m$—O—$C_1$-$C_5$ alkyl; —$(CH_2)_m$—$CO_2H$; —$(CH_2)_m$—$CO_2$—$C_1$-$C_5$ alkyl; —$(CH_2)_m$—$CONH_2$; —$(CH_2)_m$—CONH—$C_1$-$C_5$ alkyl; —CON—$(C_1$-$C_5$ alkyl$)_2$;

$R^8$ represents unsubstituted phenyl; unsubstituted pyridyl; unsubstituted phenyl-$C_1$-$C_5$ alkyl; unsubstituted pyridyl-$C_1$-$C_5$ alkyl; or mono-, di- or tri-substituted phenyl, pyridyl, phenyl-$C_1$-$C_5$ alkyl or pyridyl-$C_1$-$C_5$ alkyl, whereby the substituents independently are $C_1$-$C_5$ alkyl, $C_1$-$C_5$ alkoxy, trifluoromethyl, trifluoromethoxy, difluoromethoxy or halogen;

$R^9$ represents $C_1$-$C_5$ alkyl, $C_2$-$C_5$ alkenyl, cycloalkyl, cycloalkyl-$C_1$-$C_5$ alkyl, unsubstituted phenyl-$C_1$-$C_5$ alkyl; or mono-, di- or tri-substituted phenyl or phenyl-$C_1$-$C_5$ alkyl, whereby the substituents independently are $C_1$-$C_5$ alkyl, $C_1$-$C_5$ alkoxy, trifluoromethyl, trifluoromethoxy, difluoromethoxy or halogen;

The compounds of formula (I) can contain one or more asymmetric centres and can be present in the form of optically pure enantiomers, mixtures of enantiomers such as, for example, racemates, optically pure diastereoisomers, mixtures of diastereoisomers, diastereoisomeric racemates, mixture of diastereoisomeric racemates, or meso forms and pharmaceutically acceptable salts thereof.

In the present description the term "$C_1$-$C_5$ alkyl", alone or in combination, signifies a straight-chain or branched-chain alkyl group with 1 to 5 carbon atoms. Examples of straight-chain and branched $C_1$-$C_5$ alkyl groups are methyl, ethyl, n-propyl, isopropyl, n-butyl, n-pentyl, isobutyl, sec-butyl, tert-butyl, the isomeric pentyls, preferably methyl, ethyl, n-propyl, isopropyl, n-butyl, iso-butyl, sec-butyl, tert-butyl and n-pentyl.

The term "$C_2$-$C_5$ alkenyl", alone or in combination, signifies a straight-chain or branched-chain alkenyl group with 2 to 5 carbon atoms, preferably allyl and vinyl.

The term "$C_1$-$C_5$ alkoxy", alone or in combination, signifies a group of the general formula $C_1$-$C_5$-alkyl-O— in which "$C_1$-$C_5$-alkyl" has the previously given significance, such as methoxy, ethoxy, n-propoxy, isopropoxy, n-butoxy, isobutoxy, sec-butoxy and tert-butoxy, preferably methoxy and ethoxy.

The term "$C_2$-$C_5$ alkenyloxy", alone or in combination, signifies a group of the general formula $C_2$-$C_5$-alkenyl-O— in which "$C_2$-$C_5$-alkenyl" has the previously given significance. Preferred $C_2$-$C_5$ alkenyloxy groups are vinyloxy and allyloxy.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, cyclobutyl, cyclopentyl, cyclohexyl, cycloheptyl and cyclooctyl, preferably cyclopropyl, cyclohexyl or $C_1$-$C_5$ alkyl substituted cycloalkyl such as methyl-cyclopropyl, dimethyl-cyclopropyl, methyl-cyclobutyl, methyl-cyclopentyl, methyl-cyclohexyl, or dimethyl-cyclohexyl.

The term "aryl", alone or in combination, signifies a phenyl or naphthyl group which optionally carries one or more substituents, preferably one or two substituents, each independently selected from cyano, halogen, hydroxy, $C_1$-$C_5$ alkyl, $C_2$-$C_5$ alkenyl, $C_1$-$C_5$ alkoxy, $C_2$-$C_5$ alkenyloxy, nitro, trifluoromethyl, trifluoromethoxy, amino, carboxy, or alkoxycarbonyl such as phenyl, p-tolyl, 4-methoxyphenyl, 4-tert-butoxyphenyl, 4-fluorophenyl, 2-chlorophenyl, 4-hydroxyphenyl, 1-naphthyl and 2-naphthyl. Preferred are carboxyphenyl, $C_1$-$C_5$ alkoxy-phenyl, hydroxyphenyl and particularly phenyl.

The term "aralkyl", alone or in combination, signifies a $C_1$-$C_5$-alkyl or cycloalkyl group as previously defined in which one hydrogen atom has been replaced by an aryl group as previously defined. Preferred are benzyl and benzyl substituted in the phenyl ring with hydroxy, $C_1$-$C_5$ alkyl, trifluoromethyl, $C_1$-$C_5$ alkoxy or halogen preferably fluorine. Particularly preferred is benzyl.

For the term "heterocyclyl" and "heterocyclyl-$C_1$-$C_5$ alkyl", the heterocyclyl group is preferably a 5- to 10-membered monocyclic or bicyclic ring, which may be saturated, partially unsaturated or aromatic containing for example 1, 2 or 3 heteroatoms selected from oxygen, nitrogen and sulphur which may be the same or different. Examples of such heterocyclyl groups are pyrrolidinyl, piperidinyl, piperazinyl, morpholinyl, pyridyl, pyrimidinyl, pyrazinyl, pyridazinyl, quinolyl, isoquinolyl, thienyl, thiazolyl, isothiazolyl, furyl, imidazolyl, pyrazolyl, pyrrolyl, indazolyl, indolyl, isoindolyl, isoxazolyl, oxazolyl, quinoxalinyl, phthalazinyl, cinnolinyl, dihydropyrrolyl, pyrrolidinyl, isobenzofuranyl, tetrahydrofuranyl, dihydropyranyl. The heterocyclyl group may have up to 5, preferably 1, 2 or 3 optional substituents. Examples of suitable substituents include halogen, $C_1$-$C_5$ alkyl, amino, nitro, cyano, hydroxy, $C_1$-$C_5$ alkoxy, carboxy and $C_1$-$C_5$ alkyloxy-carbonyls.

The term "halogen" signifies fluorine, chlorine, bromine or iodine and preferably chlorine and fluorine and particularly fluorine.

The term "carboxy", alone or in combination, signifies a —COOH group.

Preferred compounds are compounds of the general formula (I) wherein n is the integer 0, 1 or 2, m is the integer 0, 1 or 2, $R^1$, $R^2$, $R^3$, $R^4$, $R^5$, $R^6$, $R^7$, $R^8$ and $R^9$ have the meaning given in the general formula (I) above and X represents oxygen and N—CN.

Other preferred compounds of the general formula (I) are those wherein n is the integer 0, m is the integer 0, $R^1$, $R^2$, $R^3$, $R^4$, $R^5$, $R^6$, $R^7$, $R^8$ and $R^9$ have the meaning given in the formula (I) above and X represents oxygen.

More preferred compounds of the general formula (I) are those wherein n is the integer 0, m is the integer 0, $R^5$ represents methyl, $R^6$ represents phenyl, $R^1$, $R^2$, $R^3$, $R^4$, $R^7$, $R^8$ and $R^9$ have the meaning given in the formula (I) above and X represents oxygen.

Examples of preferred compounds are:

1-[1-(4-Methyl-3-oxo-3,4-dihydro-quinoxalin-2-yl)-ethyl]-1-(1-phenyl-ethyl)-3-(2-propyl-phenyl)-urea;

3-Biphenyl-2-yl-1-[1-(4-methyl-3-oxo-3,4-dihydro-quinoxalin-2-yl]-1-[1-phenyl-ethyl)urea;

3-(2-Ethoxy-phenyl)-1-[1-(4-methyl-3-oxo-3,4-dihydro-quinoxalin-2-yl)-ethyl]-1-(1-phenyl-ethyl)-urea;

3-(2-Ethoxy-phenyl)-1-[(R,S)-1-(4-methyl-3-oxo-3,4-dihydro-quinoxalin-2-yl)-ethyl]-1-((S)-1-phenyl-ethyl)-urea;

3-(2-Ethoxy-phenyl)-1-[(R,S)-1-(4-methyl-3-oxo-3,4-dihydro-quinoxalin-2-yl)-ethyl]-1-((R)-1-phenyl-ethyl)-urea;

3-(2-Ethoxy-phenyl-1-(2-methoxy-(S)-1-phenyl-ethyl)-1-[(R,S)-1-(4-methyl-3-oxo-3,4-dihydro-quinoxalin-2-yl)-ethyl]-urea;
3-(2-Ethoxy-phenyl-1-(2-methoxy-(R)-1-phenyl-ethyl)-1-[(R,S)-1-(4-methyl-3-oxo-3,4-dihydro-quinoxalin-2-yl)-ethyl]-urea;
(R)-2-{3-(2-Ethoxy-phenyl)-1-[(R,S)-1-(4-methyl-3-oxo-3,4-dihydro-quinoxalin-2-yl)-ethyl]-ureido}-2-phenyl-acetamide;
(3-{1-[3-(Ethoxy-phenyl)-1-(1-phenyl-ethyl)-ureido]-ethyl}-2-oxo-2H-quinoxalin-1-yl)-acetic acid ethyl ester;
2-{3-[3-(2-Ethoxy-phenyl)-1-(1-phenyl-ethyl)-ureidom-ethyl]-2-oxo-2H-quinoxalin-1yl}-acetamide;
1-Benzyl-3-(2-ethoxy-phenyl)-1-(4-methyl-3-oxo-3,4-dihy-dro-quinoxalin-2-yl-methyl)-urea;
1-Benzyl-3-(2-ethoxy-phenyl)-1-[1-(4-methyl-3-oxo-3,4-dihydro-quinoxalin-2-yl)-ethyl]-urea;
3-(2-Ethoxy-phenyl)-1-(4-methyl-3-oxo-3,4-dihydro-quinoxalin-2-yl-methyl)-1-(1-phenyl-ethyl)-urea;
(S)-3-(2-Ethoxy-phenyl)-1-(3-oxo-3,4-dihydro-quinoxalin-2-ylmethyl)-1-(1-phenyl-ethyl)-urea;
1-(6-Chloro-pyridin-3 ylmethyl)-3 (2-ethoxy-phenyl)-1-(4-methyl-3-oxo-3,4-dihydro-quinoxalin-2ylmethyl)-urea;
(S)-3-(2-Ethoxy-phenyl)-1-(2-methoxy-1-phenyl-ethyl)-1-[1-(4-methyl-3-oxo-3,4-dihydro-quinoxalin-2-yl)-ethyl]-urea;
(R)-3-(2-Ethoxy-phenyl)-1-(2-methoxy-1-phenyl-ethyl)-1-[1-(4-methyl-3-oxo-3,4-dihydro-quinoxalin-2-yl)-ethyl]-urea;
3-(2-Ethoxy-phenyl)-1-(2-hydroxy-(S)-1-phenyl-ethyl)-1-(4-methyl-3-oxo-3,4-dihydro-quinoxalin-2-ylmethyl)-urea;
3-(2-Ethoxy-phenyl)-1-(2-methoxy-(S)-1-phenyl-ethyl)-1-(4-methyl-3-oxo-3,4-dihydro-quinoxalin-2-ylmethyl)-urea;
3-(2-Ethoxy-phenyl)-1-(3-hydroxy-(S)-1-phenyl-propyl)-1-(4-methyl-3-oxo-3,4-dihydro-quinoxalin-2-ylmethyl)-urea;
3-(2-Ethoxy-phenyl)-1-(4-methyl-3-oxo-3,4-dihydro-quinoxalin-2-ylmethyl)-1-((S)-2-phenyl-propyl)-urea;
3-(2-Ethoxy-phenyl)-1-(4-methyl-3-oxo-3,4-dihydro-quinoxalin-2-ylmethyl)-1-[-1-(3-trifluoromethyl-phenyl)-ethyl]-urea;
3-(2-Ethoxy-phenyl)-1-(4-methyl-3-oxo-3,4-dihydro-quinoxalin-2-ylmethyl)-1-[-1-(4-trifluoromethyl-phenyl)-ethyl]-urea;
N-(2-Ethoxy-phenyl)-N'-[1-(-4-methyl-3-oxo-3,4-dihydro-quinoxalin-2-yl)-ethyl)-N'-1-phenyl-ethyl-cyanoguanidine.

The present invention encompasses physiologically usable or pharmaceutically acceptable salts of compounds of formula (I). This encompasses salts with physiologically compatible mineral acids such as hydrochloric acid, sulphuric or phosphoric acid; or with organic acids such as formic acid, methanesulphonic acid, acetic acid, trifluoroacetic acid, citric acid, fumaric acid, maleic acid, tartaric acid, succinic acid or salicylic acid and the like. The compounds of formula (I) which are acidic can also form salts with physiologically compatible bases. Examples of such salts are alkali metal, alkali earth metal, ammonium and alkylammonium salts such as Na, K, Ca or tetraalkylammonium salt. For a comprehensive list see "Handbook of Pharmaceutical Salts", P. H. Stahl, C. G. Wermuth Eds., Wiley-VCH, Weinheim/Zürich 2002, p. 329-350. The compounds of formula (I) can also be present in the form of a zwitterion.

The present invention encompasses different solvation complexes of compounds of general formula (I). The solvation can be effected in the course of the manufacturing process or can take place separately, e.g. as a consequence of hygroscopic properties of an initially anhydrous compound of general formula (I).

The present invention further encompasses different morphological forms, e.g. crystalline forms, of compounds of general formula (I) and their salts and solvation complexes. Particular heteromorphs may exhibit different dissolution properties, stability profiles, and the like, and are all included in the scope of the present invention.

The compounds of formula (I) might have one or several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates and the meso-forms.

The compounds of general formula (I) and their pharmaceutically usable salts can be used as medicament for the treatment of diseases or disorders which are associated with a role of orexin comprising eating disorders, diabetes, prolactinoma, cardiovascular disorders, cancer, pain, narcolepsy, sleep disorders like insomnia, sleep apnea, parasomnia, depression, anxiety, addictions, schizophrenia, neurodegenerative disorders and dementia.

The compounds of general formula (I) can also be used in the preparation of a medicament for the treatment of disorders which are associated with a role of orexin, comprising eating disorders, sleep disorders, cardiovascular disorders, cancer, pain, depression, schizophrenia or neurodegenerative disorders.

The compounds of general formula (I) and their pharmaceutically usable salts are particularly useful for the treatment of eating disorders and sleep disorders.

Preferred compounds of formula (I) have $IC_{50}$ values below 100 nM, particularly preferred compounds have $IC_{50}$ values below 10 nM which have been determined with the FLIPR (Fluorometric Imaging Plates Reader) method described in the beginning of the experimental section.

The compounds of general formula (I) may also be used in combination with other pharmacologically active compounds comprising other orexin receptor antagonists, with lipid lowering agents, with anorectic agents, with sleep inducing agents, with antidepressants or with other drugs beneficial for the prevention or treatment of disorders as above-mentioned.

The compounds of formula (I) and their pharmaceutically usable salts can be used as medicament (e.g. in the form of pharmaceutical preparations). Hence, pharmaceutical compositions containing a compound of formula (I) and usual carrier materials and adjuvants thereof are also in the scope of the invention. These pharmaceutical compositions containing one or more compounds of formula (I) are used for the treatment of disorders which are associated with the role of orexin, comprising eating disorders and sleep disorders, cardiovascular disorders, cancer, pain, depression, schizophrenia or neurodegenerative disorders.

The pharmaceutical preparations can be administered enterally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions), or topically, e.g. in the form of ointments, creams or oils.

The compounds of formula (I) and their pharmaceutically usable salts can be processed with pharmaceutically inert, inorganic or organic adjuvants for the production of tablets, coated tablets, dragées, and hard gelatine capsules. Lactose, cornstarch or derivatives thereof, talc, stearic acid or its salts etc. can be used, for example, as such adjuvants for tablets, dragées, and hard gelatine capsules. Suitable adjuvants for soft gelatine capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilisers, wetting agents, emulsifiers, sweeteners, colorants, flavorants, salts for varying the osmotic pressure, buffers, masking agents or antioxidants. The compounds of formula (I) may also be used in combination with one or more other therapeutically useful substances. Examples are anorectic drugs like fenfluramine and related substances; lipase inhibitors like orlistat and related substances; antidepressants like fluoxetine and related substances; anxiolytics like alprazolam and related substances; sleep-inducers like zopiclone and related substances; or any other therapeutically useful substance.

Another object of the present invention is a method of treating or preventing diseases or disorders where an antagonist of a human orexin receptor is required, which comprises administering to a subject in need thereof a therapeutically effective amount of a compound of formula (I), or a pharmaceutically acceptable salt thereof.

The therapeutically effective amount of a compound of formula (I) can vary within wide limits depending on the disease to be controlled, the age and the individual condition of the patient and the mode of administration, and will, of course, be fitted to the individual requirements in each particular case. For adult patients a daily dosage of about 1 mg to 1000 mg, especially about 50 mg to about 500 mg, comes into consideration. The pharmaceutical preparations conveniently contain about 1-500 mg, preferably 5-200 mg of a compound of formula (I).

Further, the invention also relates to a process for the manufacture of pharmaceutical compositions for the treatment of disorders associated with the role of orexin, eating disorders, sleep disorders, cardiovascular disorders, cancer, pain, depression, schizophrenia or neurodegenerative disorders, containing one or more compounds of formula (I), or a pharmaceutically acceptable salt thereof, as active ingredients which process comprises mixing one or more active ingredient or ingredients with pharmaceutically acceptable excipients and adjuvants in a manner known per se.

The compounds of general formula (I) of the present invention are prepared according to the general sequence of reactions outlined in the schemes below, wherein $R^1$, $R^2$, $R^3$, $R^4$, $R^5$, $R^6$, $R^7$, $R^8$, $R^9$, $X$ and $n$ are as defined in general formula (I) above. As the case may be any compound obtained with one or more optically active carbon atoms may be resolved into pure enantiomers or diastereomers, mixtures of enantiomers or diastereomers, diastereomeric racemates and the meso-forms in a manner known per se.

The compounds obtained may also be converted into a pharmaceutically acceptable salt thereof in a manner known per se.

As shown in Scheme 1, the compounds of general formula (I) may be prepared from the corresponding 1,2-phenylenediamine derivatives with the desired 2-oxo carboxylic acid at reflux in EtOH (Lawrence D. S. et al., *J.Med.Chem.* 2001, 44, 4, 594-601; Bekerman D. G. et al., *Journal of Heterocyclic Chem.* 1992, 29, 1, 129-133). Subsequent alkylation with $R^5$—I/NaOH/TBAB (Abdel-Ghany H. et al., *Synth. Commun.*, 1990, 20, 6, 893-900) or with $R^5$—Cl/NaOEt/EtOH (Hermecz I. et al., *Heterocycles* 1998, 48, 9, 1851-1866) followed by bromination leads to the corresponding bromo intermediate. A second alkylation with the corresponding primary amine yields the secondary amine which is then converted to the desired urea compound by reaction with a commercially available or synthetized isocyanate (Scheme 1) (March J. *Advanced Organic Chemistry-Reactions, Mechanisms and Structure* 1992, page 418, 4th edition, John Wiley & Sons).

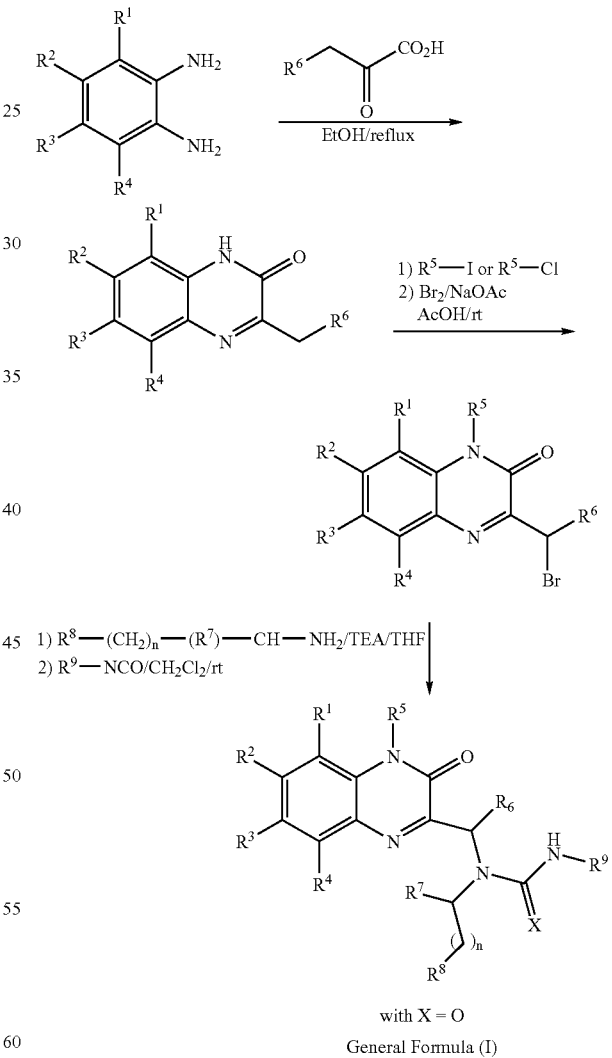

Scheme 1

General Formula (I)

The compounds of general formula (I) may be also prepared from available 1-chloro-2-nitrobenzene derivatives (cf. Scheme 2 hereinafter). Amination under basic conditions followed by the hydrogenation of the resulting nitrobenzene derivative gives the desired aniline intermediate according to the method reported (see Obase H. et al., *J. Heterocyclic Chem.* 1983, 20, 565-573). This intermediate is then converted to the corresponding quinoxalinone derivative using the same conditions as described in Scheme 1.

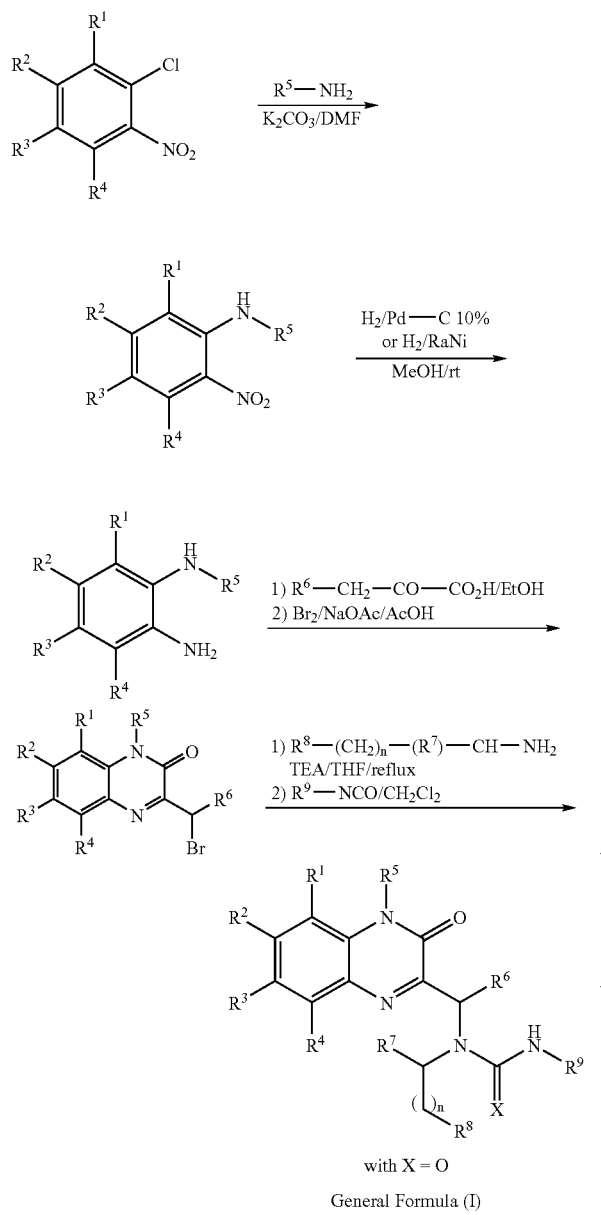

The compounds of general formula (I) wherein $R^6$ is hydrogen may also be prepared by reductive amination of 3-formyl-quinoxalin-2-one derivatives (synthetized by oxidation of the corresponding 3-methyl-quinoxalin-2-one derivative with selenium dioxide according to Ismail M. F. et al., *Ind. J. Chem.* 1981, 20B, 5, 394-397 and Farghaly A. M. et al., *Farmaco,* 1990, 45, 4, 431-438) with synthetized or commercially available primary amines (Scheme 3). The resulting secondary amine intermediate is then converted to the desired quinoxalinone derivative using the same conditions as described in Scheme 1.

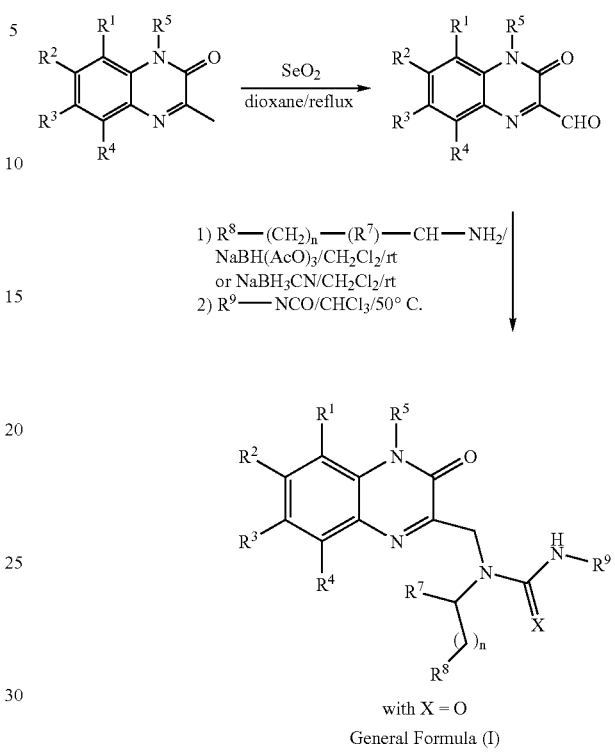

The compounds of general formula (I) wherein $R^9$ is aryl and X is N—CN (cyano-guanidine analogs) may be prepared from synthesized or commercially available isothiocyanate using known methods (Poindexter G. S. et al., WO98/54136; Atwal K. S. et al., *Tetrahedron Letters,* 1989, 30, 52, 7313-7316; Atwal K. S. et al., *J. Med. Chem.* 1995, 38, 1966-1973) (Scheme 4).

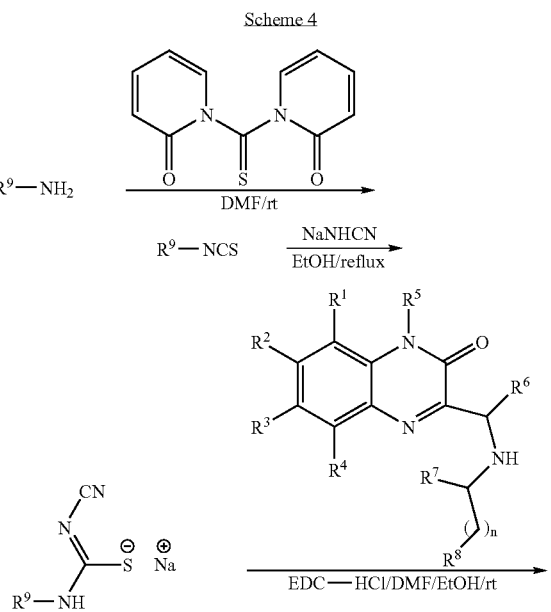

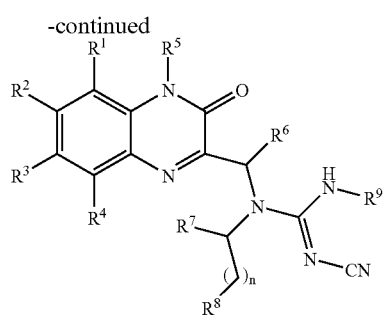

Experimental Section

I. Biology

Determination of $OX_1$ and $OX_2$ Receptor Antagonistic Activities

The $OX_1$ and $OX_2$ receptor antagonistic activity of the compounds of general formula (I) was determined in accordance with the following experimental method.

Experimental Method:

1. Intracellular Calcium Measurements

Chinese hamster ovary (CHO) cells expressing the human orexin-1 receptor or the human orexin-2 receptor, are grown in culture medium (Ham F-12 with L-Glutamine) containing 300 µg/ml G418, 100 U/ml penicillin, 100 µg/ml streptomycin and 10% inactivated foetal calf serum (FCS).

The cells were seeded at 80,000 cells/well into 96-well black clear bottom sterile plates (Costar) which had been precoated with 1% gelatine in Hanks' Balanced Salt Solution (HBSS). All reagents were from Gibco BRL.

The seeded plates are incubated overnight at 37° C. in 5% $CO_2$.

Human orexin-A as an agonist is prepared as 1 mM stock solution in methanol/water (1:1), diluted in HBSS containing 0.1% BSA and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 µl HBSS containing 2.5 mM probenecid, 0.1% BSA, 2 mM HEPES. 100 µl of that same buffer is left in each well.

Within the Fluorescent Imaging Plate Reader (FLIPR, Molecular Devices), antagonists are added to the plate in a volume of 50 µl, incubated for 20 min and finally 100 µl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. The compounds exhibit as an average an antagonistic activity regarding the $OX_1$ and $OX_2$ receptor in the range of an $IC_{50}$ of 1 nM to 100 nM.

2. In Vivo Assay:

Spontaneous Home Cage Activity and Body Temperature Measured by Radiotelemetry in Laboratory Rats:

The objective of the present test is to record the circadian behavioral activity of rats after oral administration of a compound according to general formula (I) of the invention.

Decreased home cage activity measured by telemetry in male Wistar rats was considered as an indication for sleep-inducing potential of a restricted number of quinoxalinone derivatives.

Psychotropic drugs such as antidepressants, antipsychotics, sleep inducers or psychostimulants are well known to reduce or enhance home cage activity and body temperature following oral administration to laboratory animals. Thermoregulation is a complex process that contributes to homeostasis by coordinating metabolism, energy balance and behaviour. Body temperature changes with circadian behavioural activity and increases when locomotion increases. These two parameters were measured by telemetry in conscious freely moving Wistar rats. Anaesthetized animals were implanted, under aseptic conditions, with a body temperature/activity telemetric device into the peritoneal cavity. More than two weeks after the implantation of the telemetry system, data were collected at 5 minutes intervals during 96 hours. Hourly means were calculated for each rat. The first 48 h were used as an internal control trace and drug effects were compared to vehicle placebo. This method is validated pharmacologically by measuring amplitude and time course of both hypoactivity and hypothermia induced by GABA-A receptor modulators such as zolpidem.

II. Chemistry

The following examples illustrate the preparation of pharmacologically active compounds of the invention but do not at all limit the scope thereof. All temperatures are stated in ° C.

All hydrochloride salts were prepared by dissolving the free base in dichloromethane Followed by treatment with an excess of ethereal HCl (2M).

| A. Abbreviations | |
|---|---|
| AcOEt | Ethyl acetate |
| AcOH | Acetic acid |
| BSA | Bovine serum albumin |
| br | broad (NMR) |
| CHO | Chinese hamster ovary |
| d | doublet (NMR) |
| DMAP | 4-(Dimethylamino)pyridine |
| DMF | Dimethylformamide |
| DMSO | Dimethyl sulfoxide |
| EDC-HCl | 1-(3-Dimethylaminopropyl)-3-ethylcarbodiimide hydrochloride |
| eq | equivalent |
| ES | Electron spray |
| EtOH | Ethanol |
| FC | Flash chromatography |
| FCS | Fetal calf serum |
| FLIPR | Fluorescent imaging plate reader |
| h | hour |

-continued

| A. Abbreviations | |
|---|---|
| HBSS | Hank's balanced salt solution |
| HEPES | 4-(2-Hydroxyethyl)-piperazine-1-ethanesulfonic acid |
| m | multiplet (NMR) |
| MeCN | Acetonitrile |
| MeOH | Methanol |
| Min. | minutes |
| MS | Mass spectroscopy |
| NaOAc | Sodium acetate |
| NMR | Nuclear magnetic resonance |
| LC | Liquid chromatography |
| q | quartet (NMR) |
| Ra Ni | Raney nickel |
| $R_t$ | retention time |
| rt | room temperature |
| s | singlet (NMR) |
| t | triplet (NMR) |
| TEA | Triethylamine |
| TFA | Trifluoroacetic acid |
| THF | Tetrahydrofuran |

B. 1H-quinoxalin-2-one Derivatives

1) General Procedure:

A mixture of the 1,2-phenylene-diamine derivative (1 g) and the 2-oxo-carboxylic acid derivative (1 eq) in dry EtOH (35 mL) was stirred at reflux for 2 h under nitrogen. After cooling, the EtOH was evaporated to give a crude brown solid. Recrystallisation from EtOH gave the desired quinoxalin-2-one derivative.

a) 3-Ethyl-1-methyl-1H-quinoxalin-2-one

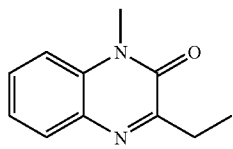

Reaction between N-methyl-1,2-phenylene-diamine and 2-oxo-butyric acid gave after recrystallisation (EtOH) the title compound;

LC-MS: $R_t$=3.81 min. m/z=189 (M+1).

$^1$H-NMR (300 MHz; CDCl$_3$) δ=1.35 (3H, t), 3.0 (2H, q), 3.7 (3H, s), 7.3 (2H, m), 7.5 (1H, t), 7.85 (1H, d).

b) 1,3-Dimethyl-1H-quinoxalin-2-one

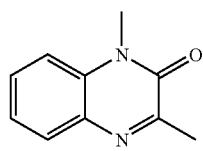

Reaction between N-methyl-1,2-phenylene-diamine and pyruvic acid gave after recrystallisation (EtOH) the title compound;

LC-MS: $R_t$=3.26 min. m/z=175 (M+1).

$^1$H-NMR (300 MHz; CDCl$_3$) δ=2.6 (3H, s), 3.7 (3H, s), 7.3 (2H, m), 7.55 (1H, t), 7.8 (1H, d).

c) 3-Ethyl-1H-quinoxalin-2-one

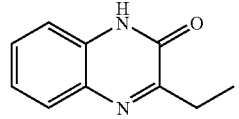

Reaction between 1,2-phenylene-diamine and 2-oxo-butyric acid gave after recrystallisation (EtOH) the title compound as a brown solid;

LC-MS: $R_t$=3.36 min. m/z=175 (M+1).

$^1$H-NMR (300 MHz; CDCl$_3$) δ=2.4 (3H, t), 3.1 (2H, q), 7.3 (2H, m), 7.5 (1H, t), 7.85 (1H, d).

d) 3-Methyl-1H-quinoxalin-2-one

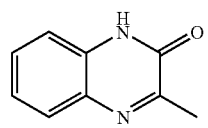

Reaction between 1,2-phenylene-diamine and pyruvic acid gave after recrystallisation (EtOH) the title compound as a beige solid;

LC-MS: $R_t$=2.91 min. m/z=161 (M+1).

$^1$H-NMR (300 MHz; DMSO-d$_6$) δ=2.4 (3H, s), 7.25 (2H, m), 7.45 (1H, m), 7.85 (1H, d), 12.25 (1H, br.s).

e) (3-Ethyl-2-oxo-2H-quinoxalin-1-yl)-acetic acid ethylester

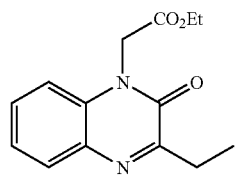

A mixture of 3-ethyl-1H-quinoxalin-2-one (1.6 g), ethyl chloroacetate (1.1 eq), NaOEt (1.1 eq) in dry EtOH (15 mL) was stirred at reflux for 16 h under nitrogen. After cooling, the reaction mixture was evaporated in vacuo to dryness, and the residue was dissolved in ether. The resulting solution was washed with saturated NaHCO$_3$ solution, water, dried (anhydrous MgSO$_4$), filtered and concentrated in vacuo to give a crude brown-orange solid.

FC (AcOEt/heptane: 7/3) gave the title compound as a brown solid.

LC-MS: $R_t$=2.91 min. m/z=261 (M+1).
$^1$H-NMR (300 MHz; CDCl$_3$) δ=1.35 (6H, m), 3.00 (2H, q), 4.25 (2H, q), 5.00 (2H, s), 7.05 (1H, d), 7.35 (1H, t), 7.55(1H, t), 7.85 (1H, d).

2) 3-Bromomethyl-1-methyl-1H-quinoxalin-2-one

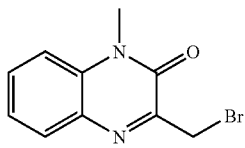

To a mixture of a 1,3-dimethyl-1H-quinoxalin-2-one (1 g), anhydrous sodium acetate (0.565 g) in glacial AcOH (10 mL) was added dropwise over 10 min. a solution of bromine (0.295 mL) in glacial AcOH (6 mL). The resulting mixture was stirred at rt under nitrogen for 2 h; then water and CH$_2$Cl$_2$ was added successively. The aqueous layer was extracted once again with CH$_2$Cl$_2$, the combined organic extracts were dried (anhydrous MgSO$_4$), filtered and concentrated to give a crude brown-orange residue.

FC (AcOEt/heptane: 1/1) gave the title compound as a pink-orange solid.

LC-MS: $R_t$=3.91 min. m/z=254 (M+1).
$^1$H-NMR (300 MHz; CDCl$_3$) δ=3.75 (3H, s), 4.7 (2H, s), 7.35 (2H, m), 7.6 (1H, m), 7.85 (1H, dd).

3) 3-(1-Bromo-ethyl)-1-methyl-1H-quinoxalin-2-one

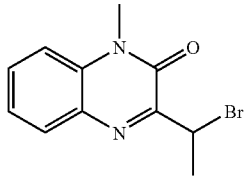

To a mixture of a 3-ethyl-1-methyl-1H-quinoxalin-2-one (1 g) and anhydrous sodium acetate (0.523 g) in glacial AcOH (10 mL) was added dropwise over 10 min. a solution of bromine (0.273 mL) in glacial AcOH (6 mL). The resulting pale yellow suspension was stirred at rt under nitrogen for 2 h, cooled to 0° C., filtered and washed with cold-water to give the title compound as a pale yellow solid.

LC-MS: $R_t$=3.91 min. m/z=268 (M+1).
$^1$H-NMR (300 MHz; CDCl$_3$) δ=2.1 (3H, t), 3.75 (3H, s), 5.7 (1H, m), 7.35 (2H, m), 7.6 (1H, m), 7.85 (1H, dd).

4) [3-(1-Bromo-ethyl)-2-oxo-2H-quinoxalin-1-yl] acetic acid ethyl ester

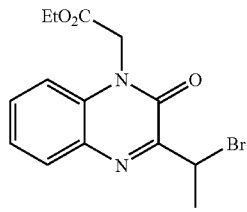

To a mixture of (3-ethyl-2-oxo-2H-quinoxalin-1-yl)-acetic acid ethylester (1 g), and anhydrous sodium acetate (0.38 g) in glacial AcOH (10 mL) was added dropwise over 10 min. a solution of bromine (0.2 mL) in glacial AcOH (6 mL). The resulting pale yellow suspension was stirred at rt under nitrogen for 2 h, combined with water/CH$_2$Cl$_2$, the aqueous layer was extracted once again with CH$_2$Cl$_2$. The combined organic extracts were dried (anhydrous MgSO$_4$), filtered and concentrated to give a crude brown-orange residue.

FC (AcOEt/n-heptane: 1/1) gave the title compound as beige solid.

LC-MS: $R_t$=2.91 min. m/z=340 (M+1).
$^1$H-NMR (300 MHz; CDCl$_3$) δ=1.25 (3H, m), 2.1 (3H, d), 4.25 (2H, q), 5.9 (1H, d), 6.2 (1H, d), 6.7 (1H, q), 7.1 (1H, d), 7.35 (1H, t), 7.55 (1H, t), 7.9 (1H, d).

5) 1-Methyl-3-[(R,S)-1-((S)-1-phenyl-ethylamino)-ethyl]-1H-quinoxalin-2-one

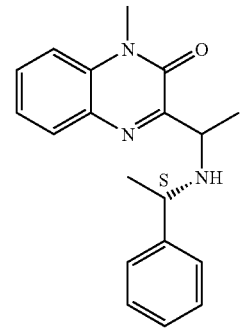

A mixture of rac-3-(1-bromo-ethyl)-1-methyl-1H-quinoxalin-2-one (0.1 g), (S)-(−)-α-methylbenzyl amine (0.049 mL), and TEA (0.052 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as a brown-orange viscous oil.

LC-MS: $R_t$=0.71 min. m/z=308 (M+1).

6) 1-Methyl-3-[(R,S)-1-((R)-1-phenyl-ethylamino)-ethyl]-1H-quinoxalin-2-one

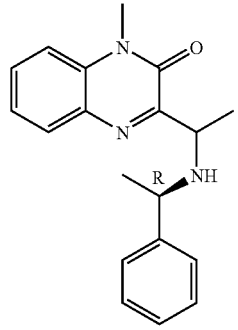

A mixture of rac-3-(1-bromo-ethyl)-1-methyl-1H-quinoxalin-2-one (0.1 g), (R)-(+)-α-methylbenzyl amine (0.049 mL), and TEA (0.052 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as an orange viscous oil.

LC-MS: R$_t$=0.71 min. m/z=308 (M+1).

7) 1-Methyl-3-[1-(1-phenyl-ethylamino)-ethyl]-1H-quinoxalin-2-one (mixture of diastereoisomers)

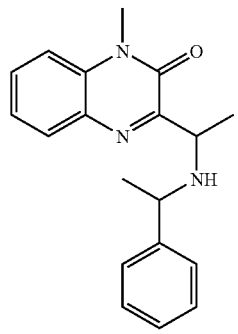

A mixture of rac-3-(1-bromo-ethyl)-1-methyl-1H-quinoxalin-2-one (0.1 g), DL (+/−)-α-methylbenzyl amine (0.049 mL), and TEA (0.052 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave 0.09 g the title compound as an orange viscous oil.

LC-MS: R$_t$=0.65 and 0.71 min. m/z=308 (M+1).

8) 3-(1-Benzylamino-ethyl)-1-methyl-1H-quinoxalin-2-one

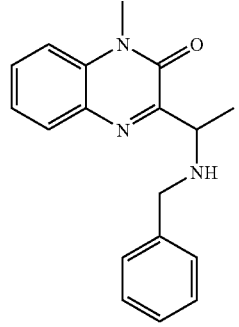

A mixture of 3-(1-bromo-ethyl)-1-methyl-1H-quinoxalin-2-one (0.1 g), benzylamine (0.041 mL), and TEA (0.052 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as an orange viscous oil.

LC-MS: R$_t$=0.69 min. m/z=294 (M+1).

9) 3-(Benzylamino-methyl)-1-methyl-1H-quinoxalin-2-one

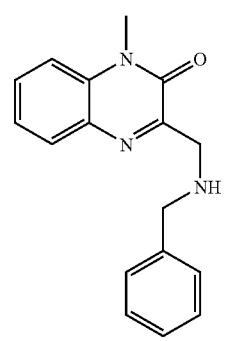

A mixture of 3-bromomethyl-1-methyl-1H-quinoxalin-2-one (0.1 g), benzylamine (0.043 mL), and TEA (0.055 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as an orange viscous oil.

LC-MS: R$_t$=0.71 min. m/z=280 (M+1).

10) (R)-1-methyl-3-[(1-phenyl-ethylamino)-methyl]-1H-quinoxalin-2-one

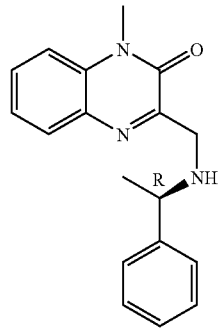

A mixture of 3-bromomethyl-1-methyl-1H-quinoxalin-2-one (0.1 g), (R)-(+)-α-methylbenzyl amine (0.05 mL), and TEA (0.055 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as an orange viscous oil.

LC-MS: R$_t$=0.69 min. m/z =294 (M+1).

11) (S)-1-methyl-3-[(1-phenyl-ethylamino)-methyl]-1H-quinoxalin-2-one

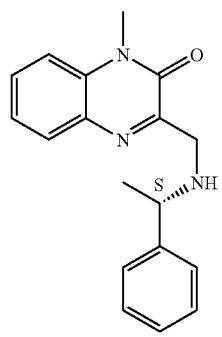

A mixture of 3-bromomethyl-1-methyl-1H-quinoxalin-2-one (0.1 g), (S)-(−)-α-methylbenzyl amine (0.05 mL), and TEA (0.055 mL) in dry THF (1 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as an orange viscous oil.

LC-MS: R$_t$=0.69 min. m/z=294 (M+1).

12) 3-[(R,S)-1-(2-Methoxy-(S)-1-phenyl-ethylamino)-ethyl]-1-methyl-1H-quinoxalin-2-one

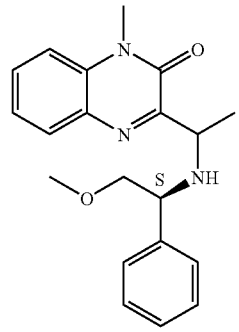

A mixture of rac-3-(1-bromo-ethyl)-1-methyl-1H-quinoxalin-2-one (0.1 g), (S)-(+)-1-amino-1-phenyl-2-methoxyethane (57 mg, 1 eq), and TEA (0.055 mL) in dry THF (2.5 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as a brown-orange viscous oil.

LC-MS: R$_t$ 2.98 min. m/z=338 (M+1).

13) 3-[(R,S)-1-(2-Methoxy-(R)-1-phenyl-ethylamino)-ethyl]-1-methyl-1H-quinoxalin-2-one

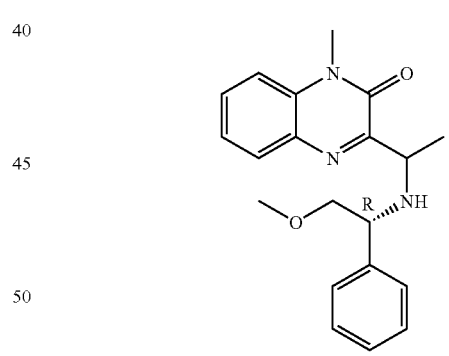

A mixture of rac-3-(1-bromo-ethyl)-1-methyl-1H-quinoxalin-2-one (0.1 g), (R)-(−)-1-amino-1-phenyl-2-methoxyethane (57 mg, 1 eq), and TEA (0.055 mL) in dry THF (2.5 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as a brown-orange viscous oil.

LC-MS: R$_t$ 2.98 min. m/z=338 (M+1).

14) {2-Oxo-3-[1-(1-phenyl-ethylamino)-ethyl]-2H-quinoxalin-1-yl}-acetic acid ethylester (mixture of diastereoisomers)

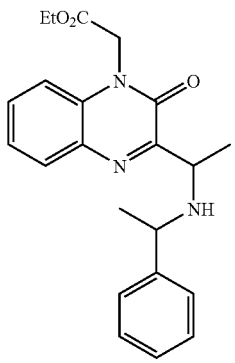

A mixture of [3-(1-bromo-ethyl)-2-oxo-2H-quinoxalin-1-yl]acetic acid ethyl ester (0.1 g), (D, L)-(+/−)-α-methylbenzylamine (35.8 mg, 1 eq), and TEA (0.041 mL) in dry THF (2.5 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as a brown-orange viscous oil.

LC-MS: R$_t$ 0.76 min. m/z=380 (M+1).

5) (R)-2-[(R,S)-1-(4-Methyl-3-oxo-3,4-dihydro-quinoxalin-2-yl)-ethylamino]-2-phenyl-acetamide

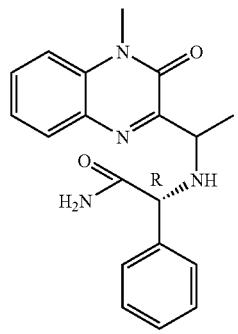

A mixture of 3-(1-bromo-ethyl)-1-methyl-1H-quinoxalin-2-one (0.1 g), (R)-(−)-2-phenylglycine amide (57 mg, 1 eq), and TEA (0.055 mL) in dry THF (2.5 mL) was stirred at reflux for 20 h under inert atmosphere. After cooling to rt, the reaction mixture was combined with water/CH$_2$Cl$_2$, and the aqueous layer was extracted once again with CH$_2$Cl$_2$. The combined organic extracts were dried (anhydrous MgSO$_4$), filtered and concentrated to give a crude brown-orange residue.

FC(CH$_2$Cl$_2$/MeOH: 9/1) gave the title compound as a pale brown viscous oil.

LC-MS: R$_t$ 2.70 min. m/z=337 (M+1).

16) 3-Oxo-3,4-dihydro-quinoxaline-2-carbaldehyde

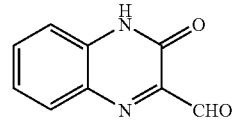

A mixture of 3-methyl-1H-quinoxalin-2-one (0.5 g) and selenium dioxide (0.728 g, 2.1 eq) in dry dioxane (33 mL) was stirred at reflux under nitrogen for 30 min. After cooling, the dark-brown mixture was concentrated under reduced pressure and the residue was purified by FC (AcOEt) to give the title compound as an orange solid.

$^1$H-NMR (300 MHz; DMSO-d$_6$) δ=7.35 (2H, m), 7.7 (1H, t), 7.9 (1H, d), 10.2 (1H, s), 12.8 (1H, br.s).

17) 4-Methyl-3-oxo-3,4-dihydro-quinoxaline-2-carbaldehyde

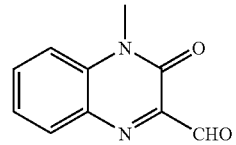

A mixture of 1,3-dimethyl-1H-quinoxalin-2-one (1 g) and selenium dioxide (1.33 g, 2.1 eq) in dry dioxane (60 mL) was stirred at reflux under nitrogen for 30 min. After cooling, the dark-brown mixture was concentrated under reduced pressure and the residue was purified by FC (AcOEt) to give the title compound as a yellow solid.

$^1$H-NMR (300 MHz; DMSO-d$_6$) δ=3.8 (3H, s), 7.35-7.45 (2H, m), 7.7 (1H, t), 8.1(1H, d), 10.5 (1H, s).

18) (S)-3-[(1-Phenyl-ethylamino)-methyl]-1H-quinoxalin-2-one

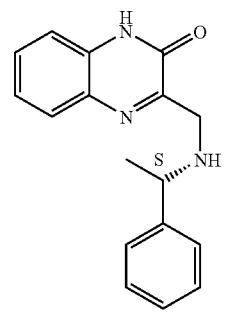

A mixture of 3-oxo-3,4-dihydro-quinoxaline-2-carbaldehyde (0.1 g), sodium triacetoxyborohydride (0.182 g, 1.5 eq), and (S)-(−)-α-methylbenzyl amine (70 mg) in dry CH$_2$Cl$_2$ (1.2 mL) was stirred at rt under nitrogen for 20 h. The reaction mixture was then poured into water, extracted CH$_2$Cl$_2$. The combined organic extracts were dried (NgSO₄), filtered and concentrated in vacuo to give a crude oil.

FC(CH₂Cl₂/MeOH: 9/1) gave the title compound as brown oil.

LC-MS: $R_t$=0.66 min. m/z=280 (M+1).

19) 3-{[(6-Chloro-pyridin-3-ylmethyl)-amino-methyl]}-1-methyl-1H-quinoxalin-2-one

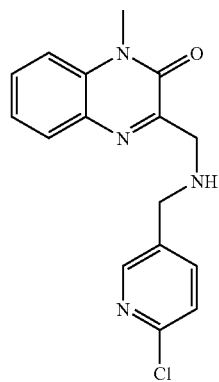

A mixture of 4-methyl-3-oxo-3,4-dihydro-quinoxaline-2-carbaldehyde (0.1 g), sodium triacetoxyborohydride (0.170 g, 1.5 eq), and 2-chloro-5-aminomethylpyridine (0.076 g, 1 eq) in dry CH₂Cl₂ (1.5 mL) was stirred at rt under nitrogen for 1 day. The orange reaction mixture was basified with a sat. NaHCO₃ solution, extracted CH₂Cl₂. The combined organic extracts were dried (MgSO₄), filtered and concentrated in vacuo to give a crude oil.

FC(CH₂Cl₂/MeOH: 9/1) gave the title compound as an orange oil.

LC-MS: $R_t$=2.93 min. m/z=315 (M+1).

20) (S)-3-[(2-Hydroxy-1-phenyl-ethylaminomethyl]-1-methyl-1H-quinoxalin-2-one

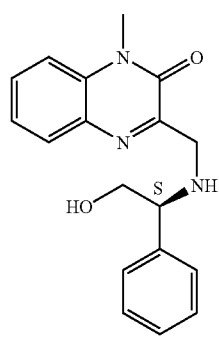

A mixture of 4-methyl-3-oxo-3,4-dihydro-quinoxaline-2-carbaldehyde (0.1 g), sodium cyanoborohydride (0.05 g, 1.5 eq), and L-(+)-α-phenylglycinol (73 mg) in dry CH₂Cl₂ (1.5 mL) was stirred at rt under nitrogen for 15 h. The reaction mixture was basified with a sat. NaHCO₃ solution, extracted CH₂Cl₂. The combined organic extracts were dried (MgSO₄), filtered and concentrated in vacuo to give a crude oil.

FC(CH₂Cl₂/MeOH: 9/1) gave the title compound as a brown solid.

LC-MS: $R_t$=0.66 min. m/z=310 (M+1).

21) (S)-3-[(-2-Methoxy-1-phenyl-ethylamino)-methyl]-1-methyl-1H-quinoxalin-2-one

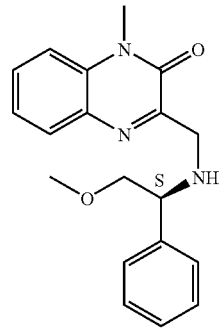

A mixture of 4-methyl-3-oxo-3,4-dihydro-quinoxaline-2-carbaldehyde (0.1 g), sodium cyanoborohydride (0.05 g, 1.5 eq), and (R)-(−)-1-amino-1-phenyl-2-methoxyethane (72 mg) in dry CH₂Cl₂ (1.5 mL) was stirred at rt under nitrogen for 16 h. The reaction mixture was basified with a sat. NaHCO₃ solution, extracted CH₂Cl₂. The combined organic extracts were dried (MgSO₄), filtered and concentrated in vacuo to give a crude oil.

FC(CH₂Cl₂/MeOH: 9/1) gave the title compound as a brown oil.

LC-MS: $R_t$=0.72 min. m/z=324 (M+1).

22) (S)-1-Methyl-3-[(2-phenyl-propylamino)-methyl]-1H-quinoxalin-2-one

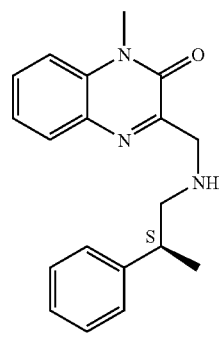

A mixture of 4-methyl-3-oxo-3,4-dihydro-quinoxaline-2-carbaldehyde (0.1 g), sodium cyanoborohydride (0.05 g, 1.5 eq), and (S)-2-phenyl-1-propylamine (80 mg) in dry CH₂Cl₂ (1.5 mL) was stirred at rt under nitrogen for 16 h. The reaction mixture was basified with a sat. NaHCO₃ solution, extracted CH₂Cl₂. The combined organic extracts were dried (MgSO₄), filtered and concentrated in vacuo to give a crude oil.

FC(CH₂Cl₂/MeOH: 9/1) gave the title compound as a brown oil.

LC-MS: $R_t$=0.75 min. m/z=308 (M+1).

23) (S)-3-[(-3-Hydroxy-1-phenyl-propylamino)-methyl]-1-methyl-1H-quinoxalin-2-one

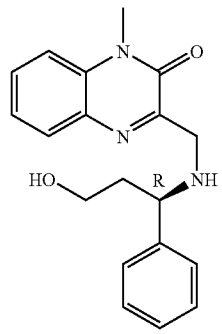

A mixture of 4-methyl-3-oxo-3,4-dihydro-quinoxaline-2-carbaldehyde (0.08 g), sodium cyanoborohydride (0.04 g, 1.5 eq), and (S)-3-amino-3-phenyl-propan-1-ol (65 mg) in dry CH$_2$Cl$_2$ (2 mL) was stirred at rt under nitrogen for 16 h. The reaction mixture was basified with a sat. NaHCO$_3$ solution, extracted CH$_2$Cl$_2$. The combined organic extracts were dried (MgSO$_4$), filtered and concentrated in vacuo to give a crude oil.

FC(CH$_2$Cl$_2$/MeOH: 9/1) gave the title compound as a yellow oil.

LC-MS: R$_t$=0.64 min. m/z=324 (M+1).

24) 1-Methyl-3-{[1-(3-trifluoromethyl-phenyl)-ethylamino]-methyl}-1H-quinoxalin-2-one (racemate)

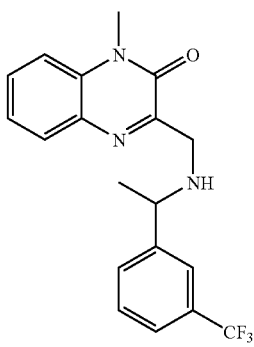

A mixture of 4-methyl-3-oxo-3,4-dihydro-quinoxaline-2-carbaldehyde (63.6 mg), sodium cyanoborohydride (0.032 g, 1.5 eq), and 1-(3-trifluoromethyl-phenyl)-ethylamine (64 mg) (Ho B. et al. *Eur. J. Med. Chem.* 2001, 36, 3, 265-286) in dry CH$_2$Cl$_2$ (1.5 mL) was stirred at rt under nitrogen for 16 h. The reaction mixture was basified with a sat. NaHCO$_3$ solution, extracted CH$_2$Cl$_2$. The combined organic extracts were dried (MgSO$_4$), filtered and concentrated in vacuo to give a crude oil.

FC(CH$_2$Cl$_2$/MeOH: 95/5) gave the title compound as a brown oil.

LC-MS: R$_t$=0.78 min. m/z=362 (M+1).

25) 1-Methyl-3-{[1-(4-trifluoromethyl-phenyl)-ethylamino]-methyl}-1H-quinoxalin-2-one (racemate)

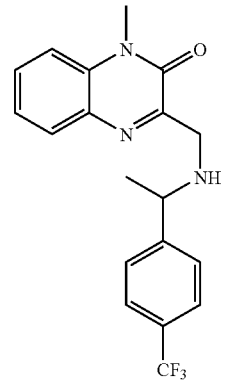

A mixture of 4-methyl-3-oxo-3,4-dihydro-quinoxaline-2-carbaldehyde (100 mg), sodium cyanoborohydride (0.050 g, 1.5 eq), and 1-(4-trifluoromethyl-phenyl)-ethylamine (100 mg) in dry CH$_2$Cl$_2$ (1.5 mL) was stirred at rt under nitrogen for 16 h. The reaction mixture was basified with a sat. NaHCO$_3$ solution, extracted CH$_2$Cl$_2$. The combined organic extracts were dried (MgSO$_4$), filtered and concentrated in vacuo to give a crude oil.

FC(CH$_2$Cl$_2$/MeOH: 95/5) gave the title compound as a brown oil.

LC-MS: R$_t$=0.77 min. m/z=362 (M+1).

EXAMPLE 1

3-(2-Ethoxy-phenyl)-1-[(R,S)-1-(4-methyl-3-oxo-3,4-dihydro-quinoxalin-2-yl)-ethyl]-1-((S)-1-phenylethyl)-urea

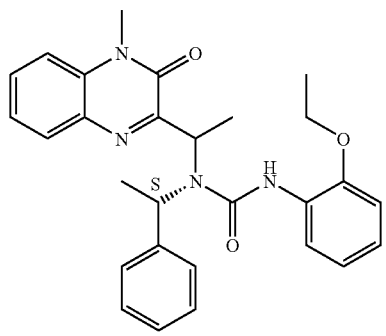

To a solution of 1-methyl-3-[(R,S)-1-((S)-1-phenyl-ethylamino)-ethyl]-1H-quinoxalin-2-one (50 mg, 0.163 mmol) in dry CHCl$_3$ (1 mL), was added 2-ethoxyphenyl isocyanate (26.3 mg, 0.163 mmol). The resulting reaction mixture was stirred at 50° C. under nitrogen for 20 h. The reaction mixture was then concentrated under reduced pressure and the residue was purified by FC(CH$_2$Cl$_2$/MeOH: 19/1) to give the title compound as a yellow foam.

LC-MS: R$_t$=1.03 min. m/z=471 (M+1).

EXAMPLE 2

3-(2-Ethoxy-phenyl)-1-[(R,S)-1-(4-methyl-3-oxo-3,4-dihydro-quinoxalin-2-yl)-ethyl]-1-((R)-1-phenyl-ethyl)-urea

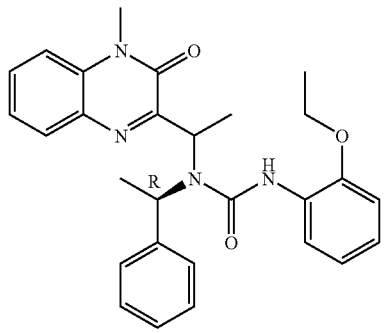

In analogy to example 1 using 1-Methyl-3-[(R,S)-1-((R)-1-phenyl-ethylamino)-ethyl]-1H-quinoxalin-2-one (1 eq).

FC(CH$_2$Cl$_2$/MeOH: 19/1) afforded the title compound as a yellow oil.

LC-MS: R$_t$=1.03 min. m/z=471 (M+1).

EXAMPLE 3

(R,S)-1-Benzyl-3-(2-ethoxy-phenyl)-1-[1-(4-methyl-3-oxo-3,4-dihydro-quinoxalin-2-yl)-ethyl]-urea

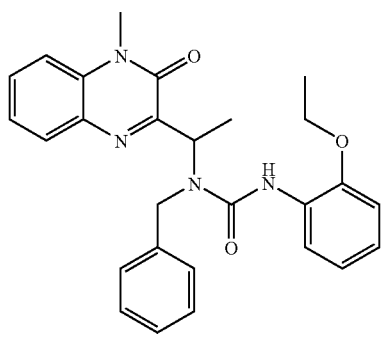

In analogy to example 1 using 3-(1-benzylamino-ethyl)-1-methyl-1H-quinoxalin-2-one (1 eq).

FC(CH$_2$Cl$_2$/MeOH: 19/1) afforded the title compound as a brown-orange oil.

LC-MS: R$_t$=1.01 min. m/z=457 (M+1).

EXAMPLE 4

1-Benzyl-3-(2-ethoxy-phenyl)-1-(4-methyl-3-oxo-3,4-dihydro-quinoxalin-2-ylmethyl)-urea

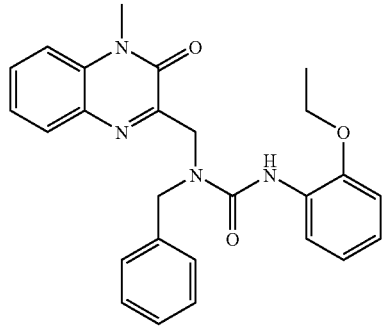

In analogy to example 1 using 3-(benzylamino-methyl)-1-methyl-1H-quinoxalin-2-one (1 eq).

FC(CH$_2$Cl$_2$/MeOH: 19/1) afforded the title compound as an orange oil.

LC-MS: R$_t$=0.98 min. m/z=443 (M+1).

EXAMPLE 5

(R)-3-(2-Ethoxy-phenyl)-1-(4-methyl-3-oxo-3,4-dihydro-quinoxalin-2ylmethyl)-1-(1-phenyl-ethyl)-urea

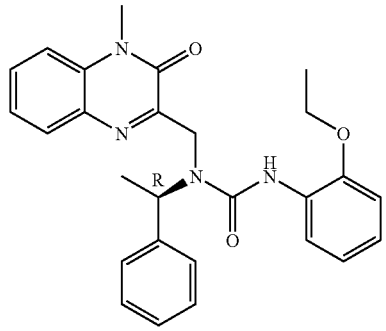

In analogy to example 1 using (R)-1-methyl-3-[(1-phenyl-ethylamino)-methyl]-1H-quinoxalin-2-one (1 eq).

FC(CH$_2$Cl$_2$/MeOH: 19/1) afforded the title compound as an orange oil.

LC-MS: R$_t$=1.00 min. m/z=457 (M+1).

EXAMPLE 6

(S)-3-(2-Ethoxy-phenyl)-1-(4-methyl-3-oxo-3,4-dihydro-quinoxalin-2ylmethyl)-1-(1-phenyl-ethyl)-urea

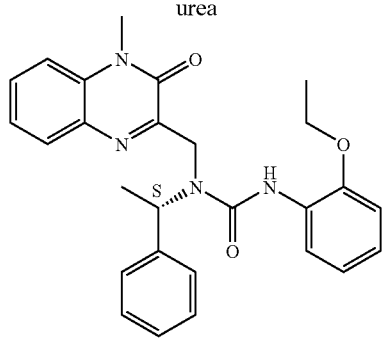

In analogy to example 1 using (S)-1-methyl-3-[(1-phenyl-ethylamino)-methyl]-1H-quinoxalin-2-one (1 eq).

FC(CH$_2$Cl$_2$/MeOH: 19/1) afforded the title compound as an orange oil.

LC-MS: R$_t$=1.00 min. m/z=457 (M+1).

EXAMPLE 7

(S)-3-(2-Ethoxy-phenyl)-1-(3-oxo-3,4-dihydro-quinoxalin-2-ylmethyl)-1-(1-phenyl-ethyl)-urea

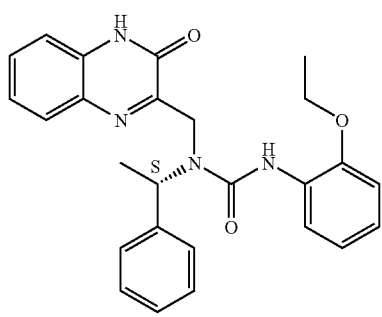

In analogy to example 1 using (S)-3-[(1-phenyl-ethylamino)-methyl]-1H-quinoxalin-2-one (1 eq)

FC(CH$_2$Cl$_2$/MeOH: 9/1) afforded the title compound as a pale-yellow solid.

LC-MS: R$_t$=0.94 min. m/z=443 (M+1).

EXAMPLE 8

1-(6-Chloro-pyridin-3ylmethyl)-3-(2-ethoxy-phenyl)-1-(4-methyl-3-oxo-3,4-dihydro-quinoxalin-2-ylmethyl)-urea

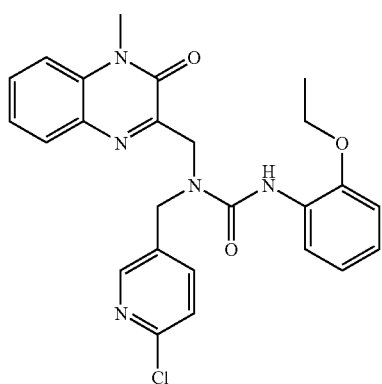

In analogy to example 1 using the 3-{[(6-chloro-pyridin-3-ylmethyl)-amino-methyl]}-1-methyl-1H-quinoxalin-2-one (1 eq)

FC(CH$_2$Cl$_2$/MeOH: 9/1) afforded the title compound as a yellow foam.

LC-MS: R$_t$=4.86 and 5.41 min. m/z=478 (M+1).

EXAMPLE 9

(R)-2-{3-(2-Ethoxy-phenyl)-1-[(R,S)-1-(4-methyl-3-oxo-3,4-dihydro-quinoxalin-2-yl)-ethyl]-ureido}-2-phenyl-acetamide

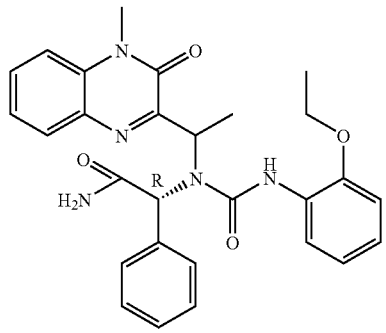

In analogy to example 1 using (R)-2-[(R,S)-1-(4-methyl-3-oxo-3,4-dihydro-quinoxalin-2-yl)-ethylamino]-2-phenyl-acetamide (1 eq).

FC (AcOEt/heptane: 7/3) afforded the title compound as white foam.

LC-MS: R$_t$=4.63 min. m/z=500 (M+1).

EXAMPLE 10

(3-{1-[3-(Ethoxy-phenyl)-1-(1-phenyl-ethyl)-ureido]-ethyl}-2-oxo-2H-quinoxalin-1-yl)-acetic acid ethyl ester (mixture of diastereoisomers)

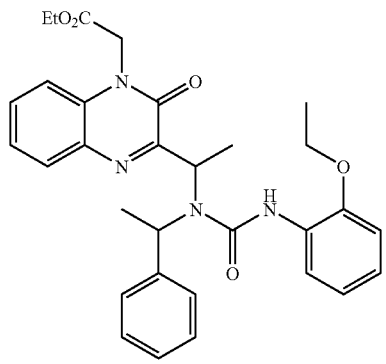

In analogy to Example 1 using {2-Oxo-3-[1-(1-phenyl-ethylamino)-ethyl]-2H-quinoxalin-1-yl}-acetic acid ethyl-ester (1 eq).

FC (AcOEt/heptane: 3/7) afforded the title compound as an orange oil.

LC-MS: R$_t$=0.95 min. m/z=543 (M+1).

EXAMPLE 11

2-(3-{1-[3-(2-Ethoxy-phenyl)-1-(1-phenyl-ethyl)-ureido]-ethyl}-2-oxo-2H-quinoxalin-1yl)-acetamide (mixture of diastereoisomers)

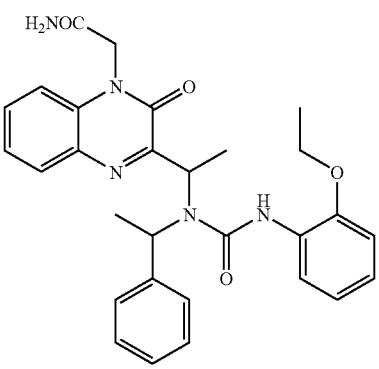

A mixture of (3-{1-[3-(2-ethoxy-phenyl)-1-(1-phenyl-ethyl)-ureido]-ethyl}-2-oxo-2H-quinoxalin-1-yl)-acetic acid ethyl ester (0.11 g), and aqueous NaOH 2N (0.5 mL, 5 eq) in a mixture MeOH/dioxane (4/3) (1.7 mL) was stirred at rt for 20 h. Then the reaction mixture was combined with water/AcOEt, the aqueous layer was acidified until pH 1-2 with aqueous HCl 2N, and extracted with $CH_2Cl_2$ (three times). The combined organic extracts were dried (anhydrous $MgSO_4$), filtered and concentrated in vacuo to give the crude acid as a white foam (0.09 g, 85%). To this crude acid (0.05 g) in dry $CH_2Cl_2$ (1.4 mL), were added successively EDC-HCl (0.026 g, 1 eq), DMAP (0.035 g, 3 eq), and a solution of ammonia (0.5 N in dioxane) (0.20 mL, 1 eq). The resulting mixture was stirred at rt under nitrogen for 20 h. The mixture was then combined with $CH_2Cl_2$/aqueous HCl 2N. The organic layer was washed twice with water, dried (anhydrous $MgSO_4$), filtered and concentrated in vacuo to give a crude oil.

FC($CH_2Cl_2$/MeOH: 9/1) afforded the title compound as a beige foam.

LC-MS: $R_t$=0.91 min. m/z=514 (M+1).

EXAMPLE 12

3-(2-Ethoxy-phenyl)-1-((R)-2-methoxy-1-phenyl-ethyl)-1-[(R,S)-1-(4-methyl-3-oxo-3,4-dihydro-quinoxalin-2-yl)-ethyl]-urea

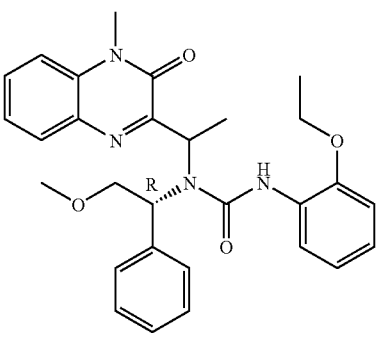

In analogy to example 1 using 3-[(R,S)-1-(2-methoxy-(R)-1-phenyl-ethylamino)-ethyl]-1-methyl-1H-quinoxalin-2-one (1 eq).

FC (AcOEt/heptane: 1/1) afforded the title compound as a pale brown oil.

LC-MS: $R_t$=5.27 min. m/z=501 (M+1).

EXAMPLE 13

3-(2-Ethoxy-phenyl)-1-((S)-2-methoxy-1-phenyl-ethyl)-1-[(R,S)-1-(4-methyl-3-oxo-3,4-dihydro-quinoxalin-2-yl)-ethyl]-urea

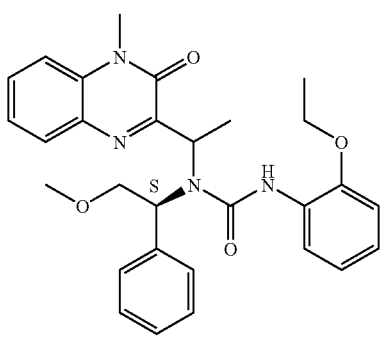

In analogy to example 1 using 3-[(R,S)-1-(2-methoxy-(S)-1-phenyl-ethylamino)-ethyl]-1-methyl-1H-quinoxalin-2-one (1 eq).

FC (AcOEt/heptane: 1/1) afforded the title compound as a pale brown oil.

LC-MS: $R_t$=5.28 min. m/z=501 (M+1).

EXAMPLE 14

3-(2-Ethoxy-phenyl)-1-((S)-2-hydroxy-1-phenyl-ethyl)-1-(4-methyl-3-oxo-3,4-dihydro-quinoxalin-2-yl-methyl)-urea

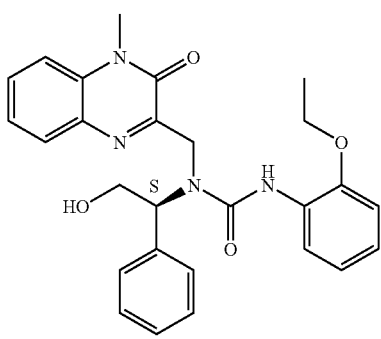

In analogy to example 1 using (S)-3-[(-2-hydroxy-1-phenyl-ethylamino)-methyl]-1-methyl-1H-quinoxalin-2-one (1 eq).

FC($CH_2Cl_2$/MeOH: 9/1) afforded the title compound as a yellow foam.

LC-MS: $R_t$=0.93 min. m/z=473 (M+1).

EXAMPLE 15

3-(2-Ethoxy-phenyl)-1-((S)-2-methoxy-1-phenyl-ethyl)-1-(4-methyl-3-oxo-3,4-dihydro-quinoxalin-2-yl-methyl)-urea

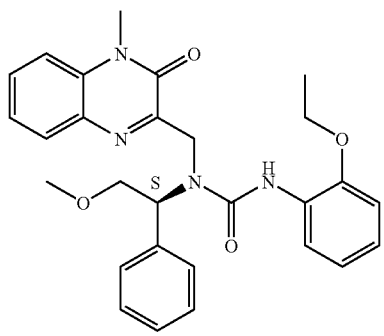

In analogy to example 1 using (S)-3-[(-2-methoxy-1-phenyl-ethylamino)-methyl]-1-methyl-1H-quinoxalin-2-one (1 eq).

FC (heptane/AcOEt: 3/7) afforded the title compound as a yellow foam.

LC-MS: $R_t$=1.00 min. m/z=487 (M+1).

EXAMPLE 16

3-(2-Ethoxy-phenyl)-1-(3-hydroxy-(S)-1-phenyl-propyl)-1-(4-methyl-3-oxo-3,4-dihydro-quinoxalin-2-yl-methyl)-urea

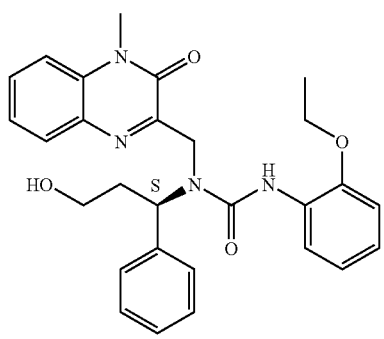

In analogy to example 1 using (S)-3-[(-3-hydroxy-1-phenyl-propylamino)-methyl]-1-methyl-1H-quinoxalin-2-one (1 eq).

FC(CH$_2$Cl$_2$/MeOH: 9/1) afforded the title compound as a yellow foam.

LC-MS: $R_t$=0.95 min. m/z=487 (M+1).

EXAMPLE 17

3-(2-Ethoxy-phenyl)-1-(4-methyl-3-oxo-3,4-dihydro-quinoxalin-2-ylmethyl)-1-((S)-2-phenyl-propyl)-urea

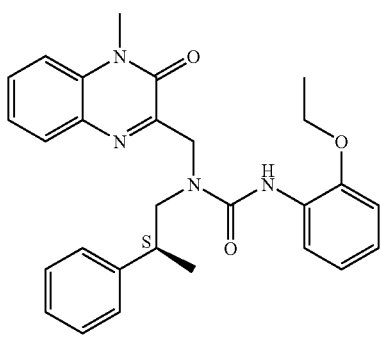

In analogy to example 1 using (S)-1-methyl-3-[(2-phenyl-propylamino)-methyl]-1H-quinoxalin-2-one (1 eq).

FC (Heptane/AcOEt: 3/7) afforded the title compound as a yellow foam.

LC-MS: $R_t$=1.03 min. m/z=471 (M+1).

EXAMPLE 18

3-(2-Ethoxy-phenyl)-1-(4-methyl-3-oxo-3,4-dihydro-quinoxalin-2-ylmethyl)-1-[-1-(3-trifluoromethyl-phenyl)-ethyl]-urea (racemate)

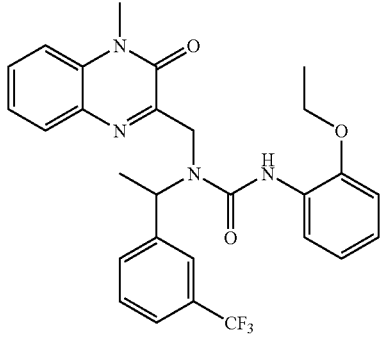

In analogy to example 1 using 1-methyl-3-{[1-(3-trifluoromethyl-phenyl)-ethylamino]-methyl}-1H-quinoxalin-2-one (1 eq).

FC (Heptane/AcOEt: 3/7) afforded the title compound as a brown oil.

LC-MS: $R_t$=1.07 min. m/z=525 (M+1).

EXAMPLE 19

3-(2-Ethoxy-phenyl)-1-(4-methyl-3-oxo-3,4-dihydro-quinoxalin-2-ylmethyl)-1-[-1-(4-trifluoromethyl-phenyl)-ethyl]-urea (racemate)

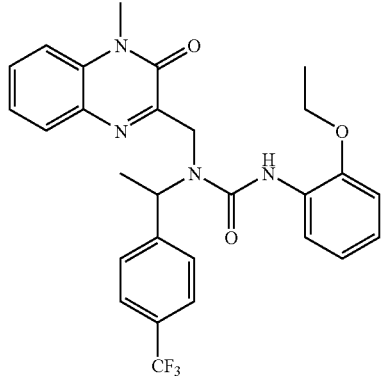

In analogy to example 1 using 1-methyl-3-{[1-(4-trifluoromethyl-phenyl)-ethylamino]-methyl}-1H-quinoxalin-2-one (1 eq).

FC (Heptane/AcOEt: 3/7) afforded the title compound as a brown oil.

LC-MS: $R_t$=1.07 min. m/z=525 (M+1). (1 eq).

EXAMPLE 20

N-(2-Ethoxy-phenyl)-N-[1-(-4-methyl-3-oxo-3,4-dihydro-quinoxalin-2-yl-ethyl)-]-N'-(1-phenyl-ethyl)-cyanoguanidine (mixture of diastereoisomers)

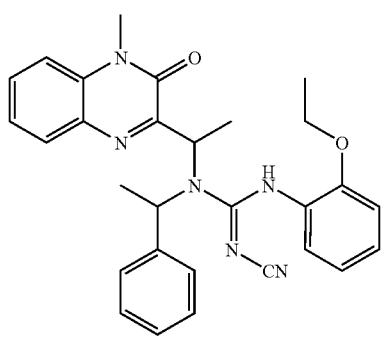

A mixture of 2-ethoxyphenyl isothiocyanate (0.1 g) and sodium hydrogencyanamide (35.7 mg, 1 eq) in dry EtOH (2 mL) was stirred at reflux under nitrogen for 3 h. After cooling to rt, EDC-HCl (0.107 g, 1 eq) and a solution of 1-methyl-3-[1-(1-phenyl-ethylamino)-ethyl]-1H-quinoxalin-2-one (0.172 g, 1 eq) in dry DMF (1 mL) were added and the resulting reaction mixture was stirred at rt under nitrogen for 20 hours. The mixture was then combined with AcOEt and sat. NaHCO$_3$, the aqueous layer was extracted once with AcOEt. The combined organic extracts were washed with brine, dried (anhydrous MgSO$_4$), filtered and concentrated to give a crude pale-brown oil.

FC (AcOEt/heptane: 7/3) gave the title compound as a white solid.

LC-MS: $R_t$=5.26 min. m/z=495 (M+1).

The invention claimed is:

1. A compound of formula (I)

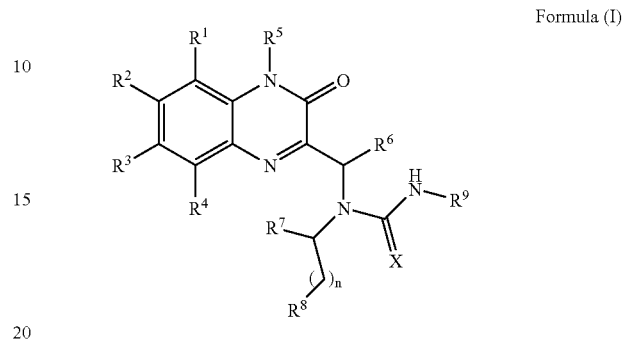

Formula (I)

wherein:
X is O;
n is the integer 0;
m is the integer 0, 1, 2, or 3;
$R^1$, $R^2$, $R^3$, $R^4$ represent hydrogen;
$R^5$ represents hydrogen, $C_1$-$C_5$ alkyl, —(CH$_2$)$_m$—CO$_2$-$C_1$-$C_5$ alkyl, —(CH$_2$)$_m$—CONH$_2$, —(CH$_2$)$_m$—CONH—$C_1$-$C_5$ alkyl, or —CON—($C_1$-$C_5$ alkyl);
$R^6$ represents hydrogen, or $C_1$-$C_5$ alkyl;
$R^7$ represents hydrogen; $C_1$-$C_5$ alkyl; $C_2$-$C_5$ alkenyl; or mono-, di- or tri-substituted phenyl or phenyl-$C_1$-$C_5$ alkyl, whereby the substituents independently are $C_1$-$C_5$ alkyl, $C_1$-$C_5$ alkoxy, $C_2$-$C_5$ alkenyl or halogen; —(CH$_2$)$_m$—OH; —(CH$_2$)$_m$—O—$C_1$-$C_5$ alkyl; —(CH$_2$)$_m$—CO$_2$H; —(CH$_2$)$_m$—CO$_2$—$C_1$-$C_5$ alkyl; —(CH$_2$)$_m$—CONH$_2$; —(CH$_2$)$_m$—CONH—$C_1$-$C_5$ alkyl; or —CON—($C_1$-$C_5$ alkyl)$_2$;
$R^8$ represents unsubstituted phenyl; or mono-, di- or tri-substituted phenyl, whereby the substituents independently are $C_1$-$C_5$ alkyl, $C_1$-$C_5$ alkoxy, trifluoromethyl, trifluoromethoxy, difluoromethoxy or halogen; and
$R^9$ represents mono-, di- or tri-substituted phenyl whereby the substituents independently are $C_1$-$C_5$ alkyl, $C_1$-$C_5$ alkoxy, trifluoromethyl, trifluoromethoxy, difluoromethoxy or halogen;
or an optically pure enantiomer, a mixture of enantiomers, a racemate, an optically pure diastereoisomer, a mixture of diastereoisomers, a diastereoisomeric racemate, a mixture of diastereoisomeric racemates, or a meso form, or a pharmaceutically acceptable salt thereof.

2. The compound of formula (I) according to claim 1, wherein n is the integer 0, m is the integer 0, and X represents oxygen; or a pharmaceutically acceptable salt therof.

3. The compound of formula (I) according to claim 1, wherein n is the integer 0, m is the integer 0, $R^5$ represents methyl, $R^6$ represents phenyl, and X represents oxygen; or a pharmaceutically acceptable salt therof.

4. The compound according to claim 1 selected from the group consisting of:
1-[1-(4-Methyl-3-oxo-3,4-dihydro-quinoxalin-2-yl)-ethyl]-1-(1-phenyl-ethyl)-3-(2-propyl-phenyl)-urea;
3-(2-Ethoxy-phenyl)-1-[1-(4-methyl-3-oxo-3,4-dihydro-quinoxalin-2-yl)-ethyl]-1-(1-phenyl-ethyl)-urea;
3-(2-Ethoxy-phenyl)-1-[(R,S)-1-(4-methyl-3-oxo-3,4-dihydro-quinoxalin-2-yl)-ethyl]-1-((S)-1-phenyl-ethyl)-urea;

3-(2-Ethoxy-phenyl)-1-[(R,S)-1-(4-methyl-3-oxo-3,4-dihydro-quinoxalin-2-yl)-ethyl]-1-((R)-1-phenyl-ethyl)-urea;

3-(2-Ethoxy-phenyl-1-(2-methoxy-(S)-1-phenyl-ethyl)-1-[(R,S)-1-(4-methyl-3-oxo-3,4-dihydro-quinoxalin-2-yl)-ethyl]-urea;

3-(2-Ethoxy-phenyl)-1-(2-methoxy-(R)-1-phenyl-ethyl)-1-[(R,S)-1-(4-methyl-3-oxo-3,4-dihydro-quinoxalin-2-yl)-ethyl]-urea;

(R)-2-{3-(2-Ethoxy-phenyl)-1-[(R,S)-1-(4-methyl-3-oxo-3,4-dihydro-quinoxalin -2-yl)-ethyl]-ureido}-2-phenyl-acetamide;

(3-{1-[3-(Ethoxy-phenyl)-1-(1-phenyl-ethyl)-ureido]-ethyl}-2-oxo-2H-quinoxalin-1-yl)-acetic acid ethyl ester;

2-{3-[3-(2-Ethoxy-phenyl)-1-(1-phenyl-ethyl)-ureidomethyl]-2-oxo-2H-quinoxalin-1yl}-acetamide;

1-Benzyl-3-(2-ethoxy-phenyl)-1-(4-methyl-3-oxo-3,4-dihydro-quinoxalin-2-yl-methyl)-urea;

1-Benzyl-3-(2-ethoxy-phenyl)-1-[1-(4-methyl-3-oxo-3,4-dihydro-quinoxalin-2-yl)-ethyl]-urea;

3-(2-Ethoxy-phenyl)-1-(4-methyl-3-oxo-3,4-dihydro-quinoxalin-2-yl-methyl)-1-(1-phenyl-ethyl)-urea;

(S)-3-(2-Ethoxy-phenyl)-1-(3-oxo-3,4-dihydro-quinoxalin-2-ylmethyl)-1-(1-phenyl-ethyl)-urea;

(S)-3-(2-Ethoxy-phenyl)-1-(2-methoxy-1-phenyl-ethyl)-1-[1-(4-methyl-3-oxo -3,4-dihydro-quinoxalin-2-yl)-ethyl]-urea;

(R)-3-(2-Ethoxy-phenyl)-1-(2-methoxy-1-phenyl-ethyl)-1-[1-(4-methyl-3-oxo-3,4-dihydro-quinoxalin-2-yl)-ethyl]-urea;

3-(2-Ethoxy-phenyl)-1-(2-hydroxy-(S)-1-phenyl-ethyl)-1-(4-methyl-3-oxo-3,4-dihydro-quinoxalin-2-ylmethyl)-urea;

3-(2-Ethoxy-phenyl)-1-(2-methoxy-(S)-1-phenyl-ethyl)-1-(4-methyl-3-oxo-3,4-dihydro-quinoxalin-2-ylmethyl)-urea;

3-(2-Ethoxy-phenyl)-1-(3-hydroxy-(S)-1-phenyl-propyl)-1-(4-methyl-3-oxo-3,4-dihydro-quinoxalin-2-ylmethyl)-urea;

3-(2-Ethoxy-phenyl)-1-(4-methyl-3-oxo-3,4-dihydro-quinoxalin-2-ylmethyl)-1-[-1-(3-trifluoromethyl-phenyl)-ethyl]-urea; and 3-(2-Ethoxy-phenyl)-1-(4-methyl-3-oxo-3,4-dihydro-quinoxalin-2-ylmethyl)-1-[-1-(4-trifluoromethyl-phenyl)-ethyl]-urea;

or a pharmaceutically acceptable salt of such a compound.

5. A pharmaceutical composition comprising one or more compounds of claim 1, or a pharmaceutically acceptable salt thereof, and a carrier and/or adjuvant.

6. A pharmaceutical composition comprising one or more compounds of claim 4, or a pharmaceutically acceptable salt thereof, and a carrier and/or adjuvant.

\* \* \* \* \*